United States Patent [19]

Michl et al.

[11] Patent Number: 4,921,977

[45] Date of Patent: May 1, 1990

[54] OBTAINING MALEIC ANHYDRIDE NOT PRONE TO DISCOLOR

[75] Inventors: Gerhard Michl, Ludwigshafen; Rolf Seubert, Frankenthal; Johannes E. Schmidt, Ludwigshafen, all of Fed. Rep. of Germany

[73] Assignee: BASF Aktiengesellschaft, Ludwigshafen, Fed. Rep. of Germany

[21] Appl. No.: 293,448

[22] Filed: Jan. 4, 1989

[30] Foreign Application Priority Data

Jan. 8, 1988 [DE] Fed. Rep. of Germany ....... 3800308

[51] Int. Cl.$^5$ .......................................... C07D 307/60
[52] U.S. Cl. .................................. 549/256; 549/257; 549/262
[58] Field of Search .................. 549/262, 256, 257

[56] References Cited

U.S. PATENT DOCUMENTS

| 3,041,251 | 6/1962 | Perfetti et al. | 549/262 |
| 3,622,600 | 11/1971 | Feder | 549/262 |
| 3,965,126 | 6/1976 | Wirth et al. | 260/346.8 M |
| 4,260,546 | 4/1981 | Schroeder et al. | 549/262 |
| 4,675,420 | 6/1987 | Block et al. | 549/257 |

FOREIGN PATENT DOCUMENTS 2008619 9/1970 Fed. Rep. of Germany .
1204846 9/1970 United Kingdom .

OTHER PUBLICATIONS

Vogler et al., *J. of Chemical and Engineering Data*, vol. 8, No. 4, pp. 620–623, Oct. 1963.

*Primary Examiner*—Mary C. Lee
*Assistant Examiner*—Bernard I. Dentz
*Attorney, Agent, or Firm*—Keil & Weinkauf

[57] ABSTRACT

Process for obtaining maleic anhydride that is not prone to discolor by treating crude maleic anhydride with oxygen, a gas mixture containing oxygen, or a substance that releases oxygen before or while it is distilled.

3 Claims, No Drawings

OBTAINING MALEIC ANHYDRIDE NOT PRONE TO DISCOLOR

The present invention relates to a process for obtaining maleic anhydride that is not prone to discolor from crude maleic anhydride by fractional distillation.

It is well known that maleic anhydride is prepared by the catalytic oxidation of benzene, naphthenes, butenes, or butane in the vapor phase, and that it is also obtained as a by-product of the preparation of phthalic anhydride by oxidation of o-xylene or naphthalene. It is usual to isolate maleic anhydride from the crude product by fractional distillation; crystallization of the distillate gives colorless, almost pure maleic anhydride. It has been found however that even the colorless, crystalline maleic anhydride obtained in this way is prone to discolor when it is stored for some time, and molten maleic anhydride discolors quicker.

Since such discoloration can be a considerable disadvantage in subsequent use, above all in applications such as the manufacture of unsaturated polyester resins or alkyd resins, it has already been suggested that, inter alia, maleic anhydride whose color is not stable should be converted by chemical treatment into very pure maleic anhydride that is not prone to discolor. Thus in GB-PS 1 204 846 it is said that, for instance, dibenzyl sulfide is added to distilled maleic anhydride, and it is known from DE-OS 20 08 619 that a product of stable color is obtained by passing molten maleic anhydride over certain inorganic salts, for example barium chloride.

Treating maleic anhydride with the chemical additives mentioned involves employing extra technical resources and also has the disadvantage that it introduces further impurities. A process that would avoid these disadvantages but provide very pure maleic anhydride of stable color was therefore sought.

We have found that if the crude maleic anhydride is treated with oxygen, a gas mixture containing oxygen, or a substance that releases oxygen, either before or during the distillation, the isolation of maleic anhydride by fractional distillation of the crude substance yields a very pure product that is not prone to discolor.

In the novel process one starts with crude maleic anhydride obtained in the usual way, for instance by the catalytic oxidation of benzene, naphthenes, phenol, furan, 1-butene, 2-butene, butane, o-xylene, or naphthalene. Particularly advantageous results are obtained by employing crude maleic anhydride recovered from the waste water that arises when phthalic anhydride is produced by air oxidation of o-xylene or naphthalene as described in, for instance, DE-PS 2 356 049.

The crude maleic anhydride obtained from one of the syntheses mentioned above contains from 80% to 99% of the pure compound, the remainder consisting of other compounds formed in the process, such as phthalic anhydride, citraconic anhydride, benzoic acid, quinones, etc. It is subjected to conventional fractional distillation, either continuously or batchwise, which removes low-boiling and high-boiling fractions; the pure maleic anhydride is conveniently taken off as a liquid or vapor fraction through a side outlet of the column. If the distillation plant consists of two columns, pure maleic anhydride is taken from the head of the second column.

The novel step consists in treating the crude maleic anhydride with oxygen, a gas containing oxygen, or a substance that releases oxygen, either before it is distilled or while it is being distilled. A gas containing oxygen can be used instead of pure oxygen, and the use of air is preferred. A suitable substance that releases oxygen is hydrogen peroxide solution, for example. The ratio of oxygen to crude maleic anhydride may be from 0.15 mmol/mol to 30 mmol/mol, for example; preferably it is from 1 mmol/mol to 15 mmol/mol. The oxygen treatment is carried out at a temperature of from 40° C. to 220° C., preferably from 60° C. to 180° C.

A convenient method of treating crude maleic anhydride with oxygen is to pass air into the molten substance. For this purpose it is recommended that a conventional gas-liquid reactor or gas-liquid mixer should be installed between the storage tank for crude maleic anhyride and the distillation column. Temperatures of from 60° C. to 180° C. are usually chosen for this oxygen treatment, which can be carried out under atmospheric pressure, slightly reduced pressure, or slightly increased pressure.

It is also possible to lead air or the oxygen-releasing compound into the distillation column, together with the crude maleic anhydride. The separation of low-boiling and high-boiling fractions then takes place while the novel purification of the maleic anhydride is being carried out. The temperatures in the distillation column are approximately from 100° C. to 180° C. Oxygen treatment in the distillation column is usually carried out in vacuo.

Surprisingly, outstandingly high-quality maleic anhydride, which excels particularly by virtue of its stable color, is obtained by the novel process.

EXAMPLE 1 (COMPARISON)

Crude maleic anhydride recovered from waste water arising from the production of phthalic anhydride by the air oxidation of o-xylene was fed at a temperature of 90° C. to the 10th plate of a fractionating column at the rate of 2.2 kg/h; the mass fractions of the components of the crude substance were 87.5% of maleic anhydride, 3.0% of citraconic anhydride, 2.5% of phthalic anhydride, 3.5% of benzoic acid, and 3.5% of miscellaneous impurities. The 50-plate column had a diameter of 80 mm; it was operated with a head pressure of 100 mbar.

The measured total rate of condensation (condensation temperature 70° C.) at the head of the column was 7.5 kg/h; the take-off rate at the head was 0.07 kg/h, and the reflux rate was 7.4 kg/h. The mass fraction of maleic anhydride in the distillate taken from the head was 99.98%.

Bottoms (at a temperature of 170° C.) were removed at the rate of 0.30 kg/h. The mass fractions of the components in this mixture was 27.0% of maleic anhydride, 18.0% of citraconic anhydride, 23.0% of phthalic anhydride, and 27.5% of benzoic acid; the remainder consisted of miscellaneous impurities, including high-boiling hydrocarbons, organic acids of high molecular weight, and decomposition products.

Liquid maleic anhydride at a temperature of 130° C. was taken from the 40th plate via a side outlet at the rate of 1.8 kg/h. The platinum-cobalt color of this melt was from 5 to 10. After about 48 h in the storage tank the platinum-cobalt color of the melt was found to be from 40 to 60.

EXAMPLE 2

Crude maleic anhydride was distilled as described in Example 1 except that air was introduced into the fractionating column at the rate of 7 l/h, together with the crude maleic anhydride.

The platinum-cobalt color of the melt obtained from the side outlet of the column was from 5 to 10. Even after storage for several days the value of the platinum-cobalt color of the melt had not increased.

We claim:

1. In a process for obtaining maleic anhydride that is not prone to discolor from crude maleic anhydride by fractional distillation wherein the crude maleic anhydride is recovered from waste water arising from the production of phthalic anhydride by air oxidation of o-xylene or naphthalene, the improvement which comprises: treating the crude maleic anhydride with air, either before or during the distillation.

2. A process as described in claim 1 wherein the treatment of crude maleic anhydride is carried out at a temperature of from 40° C. to 220° C.

3. A process as described in claim 1 wherein the ratio of oxygen in the air to crude maleic anhydride is from 0.15 mmol/mol to 30 mmol/mol.

* * * * *